(12) United States Patent
Walz et al.

(10) Patent No.: US 9,278,929 B1
(45) Date of Patent: Mar. 8, 2016

(54) SYNTHESIS OF INTERMEDIATE ANILINO METHYL ESTERS USED IN THE PRODUCTION OF SYNTHETIC OPIOID ANALGESICS

(71) Applicant: U.S. Army Edgewood Chemical and Biological Command, Washington, DC (US)

(72) Inventors: Andrew J Walz, Baltimore, MD (US); Fu-Lian Hsu, Potomac, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 25 days.

(21) Appl. No.: 14/286,330

(22) Filed: May 23, 2014

Related U.S. Application Data

(62) Division of application No. 13/773,094, filed on Feb. 21, 2013, now Pat. No. 8,742,111.

(51) Int. Cl.
C07D 211/56 (2006.01)
C07D 211/66 (2006.01)

(52) U.S. Cl.
CPC .................................. *C07D 211/66* (2013.01)

(58) Field of Classification Search
CPC ....................................................... C07D 211/56
USPC ............................................................ 546/224
See application file for complete search history.

(56) References Cited

U.S. PATENT DOCUMENTS

| | | | | |
|---|---|---|---|---|
| 5,763,652 A | * | 6/1998 | Kawabe et al. | ............... 562/512 |
| 8,779,167 B2 | * | 7/2014 | Ma et al. | ....................... 549/292 |
| 2008/0319196 A1 | * | 12/2008 | Cheng | ........................... 546/224 |

OTHER PUBLICATIONS

Trifluoro Acetic Acid, Wikipedia p. 1-2 (2014).*
Trifluoroacetic acid "Fisher Scientitic" p. 1-3 (2015).*

* cited by examiner

*Primary Examiner* — Celia Chang
(74) *Attorney, Agent, or Firm* — Ulysses John Biffoni

(57) ABSTRACT

An improved process or method of synthesis of carfentanil and other potent opioid analgesics of the N-alkyl 4-substituted 4-piperdinylamide class which can be used as morphine substitutes.

5 Claims, No Drawings

SYNTHESIS OF INTERMEDIATE ANILINO METHYL ESTERS USED IN THE PRODUCTION OF SYNTHETIC OPIOID ANALGESICS

CROSS-REFERENCE TO RELATED APPLICATIONS

This application is a divisional of application Ser. No. 13/773,094 filed on Feb. 21, 2013, now U.S. Pat. No. 8,742,111 which is commonly assigned.

GOVERNMENT INTEREST

The invention described herein may be manufactured, used, and/or licensed by or for the United States Government.

FIELD OF THE INVENTION

The invention is directed to a new synthesis of an intermediate anilino methyl ester which is employed in the synthesis of Carfentanil, Sufentanil, Alfentanil, and Remifentanil.

BACKGROUND OF THE INVENTION

4-Anilidopiperidine analgesics developed by Janssen Pharmaceuticals are a class of clinically important synthetic opiates. These include Carfentanil, Sufentanil, Alfentanil, and Remifentanil.

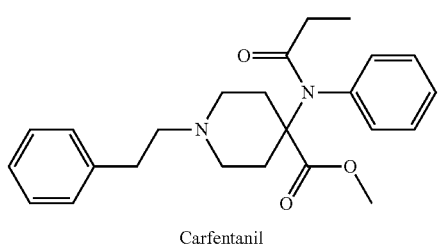
Carfentanil

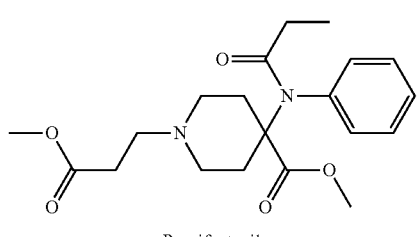
Remifentanil

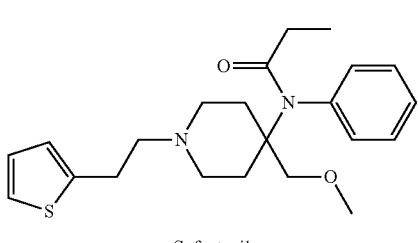
Sufentanil

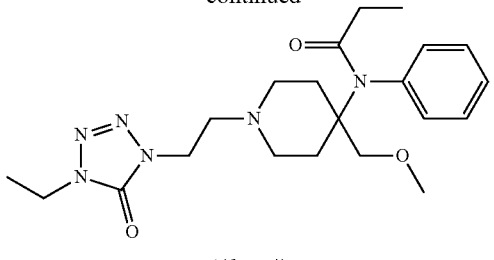
Alfentanil

The syntheses of these compounds have been disclosed in the patent and open literature. A partial general synthetic scheme is shown below.

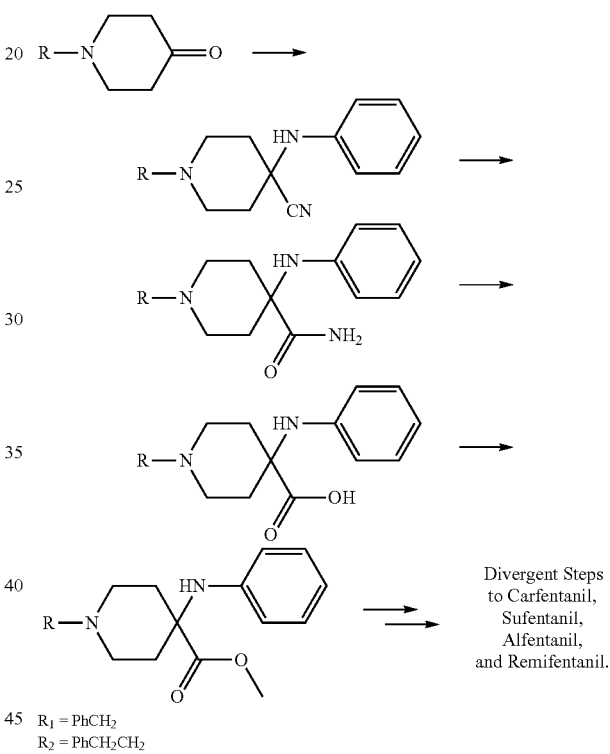

$R_1 = PhCH_2$
$R_2 = PhCH_2CH_2$

With $R_1$=PhCH$_2$, commercially available 1-benzyl-4-piperidinone is subjected to a Strecker reaction with aniline to form an amino nitrile. The conversion of the nitrile group to the methyl ester occurs as follows. The nitrile is converted to an amide under strongly acidic conditions. The amide is then converted to a carboxylic acid under strongly basic conditions. The resulting acid is then converted to the intermediate anilino methyl ester either via carboxylic acid or its sodium salt. The intermediate anilino methyl ester can be transformed, after numerous divergent steps, into Carfentanil, Sufentanil, Alfentanil, or Remifentanil.

With $R_2$=PhCH$_2$CH$_2$, the yield of the hydrolysis of the nitrile under high acidic conditions, e.g. sulfuric acid, to the corresponding amide is very low (about 14% or less). Non-acidic conditions also yield less than satisfactory results.

In U.S. Pat. No. 5,106,983 (Reiff, et al.), 4-anilidopiperidine analgesics as above described are produced by the series of reactions as noted above including a Strecker synthesis to give an aminonitrile and the nitrile is then converted to a formamide with formic acid and acetic anhydride. This compound is hydrolyzed to an imidate with refluxing methanolic hydrogen chloride. Decomposition of this in dilute base gives an amide. The net yield for these three steps which substitutes for the acid hydrolysis of the nitrile is about 47%. This three step procedure to replace the sulfuric acid hydrolysis is tedious.

SUMMARY OF THE INVENTION

It is an object of this invention to provide an improved process for synthesis of 4-anilidopiperidine analgesics and, in particular, an improved method for synthesizing certain intermediates of such synthesis.

It has been found that the conversion of the aminonitrile to the corresponding amide can be improved by substituting a portion of the sulfuric acid with a weaker, more volatile acid. The synthesis also employs a cyclizing reagent and spiro intermediate in the transformation of the amide into the intermediate aniline methyl ester.

DETAILED DESCRIPTION OF THE INVENTION

This invention relates to the synthesis of 4-anilidopiperidine analgesics, such as Carfentanil, Sufentanil, Alfentanil, and Remifentanil and, in particular, to the intermediates used in forming such compounds. The new synthesis of the intermediates is shown below. The first reaction is a Strecker reaction between 1-benzyl-4-piperidinone with aniline to form an aminonitrile (1). The nitrile is then converted to the amide (2) with a mixture of an organic acid and a non-aqueous inorganic acid, e.g., trifluoroacetic acid and sulfuric acid, via indirect acid catalyzed hydration. The organic acid acts as an acidic solvent. Sulfuric acid can be replaced with methanesulfonic acid. Molar ratios of the sulfuric acid to the organic acid will range from about 1:10 to 1:2, with about 1:4 being preferred. The amide (2) is cyclized to a 2,4-diaza-4-oxo-cyclopentane piperidine (3). A particularly useful cyclizing agent is dimethylformamide dimethoxy acetal. The 2,4-diaza-4-oxo-cyclopentane piperidine (3) is converted to the corresponding methyl ester (4) by reaction with sulfuric acid in methanol.

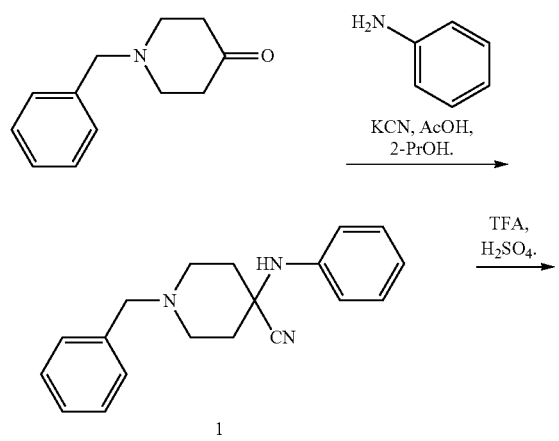

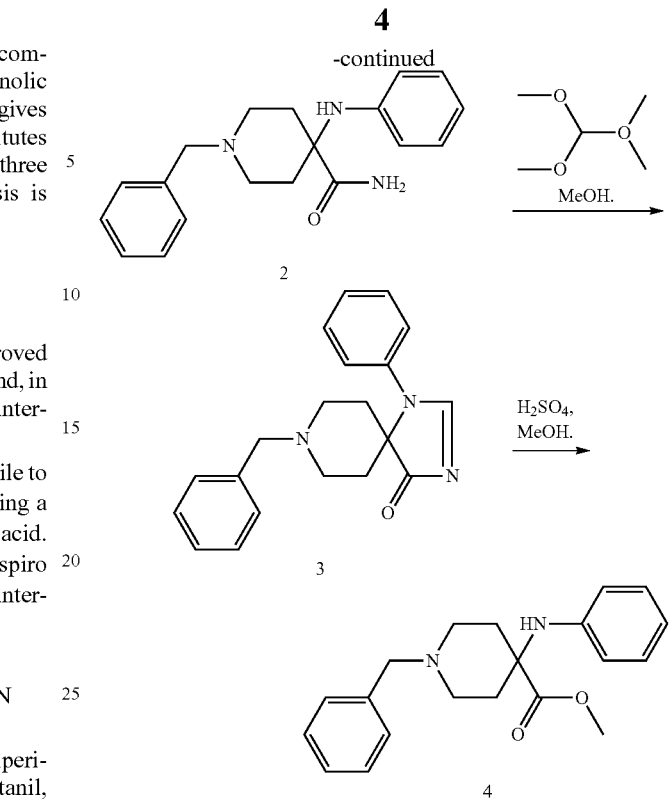

EXAMPLE 1

4-(Phenylamino)-1-(phenylmethyl)-4-piperidinenitrile, 1

1-Phenylmethyl-4-piperidinone (20.00 g, 0.106 mol), KCN (9.60 g, 0.147 mol), and aniline (13.60 g, 0.146 mol) in 180 mL isopropanol were cooled in an ice bath. Acetic acid (20 mL) was added dropwise and the addition funnel was rinsed with 20 mL isopropanol. The solution was heated at reflux for 4 h. The mixture was allowed to cool to room temperature and poured over an ice (120 g)/concentrated ammonium hydroxide (80 mL) mixture. The aqueous solution was extracted three times with chloroform. The organic layer was washed with brine. The organic solution was dried with $MgSO_4$, filtered, and the volatiles were evaporated. The residue was recrystallized from isopropanol to provide 24.04 g of a white solid in a 78% yield. mp 145-147° C.; $^1$H NMR ($CDCl_3$) δ 7.35-7.23 (m, 6H), 6.93-6.90 (m, 4H), 3.65, (br s, 1H), 3.56 (br s, 2H), 2.81 (br d, 2H, J=11.91 Hz), 2.46 (t, 2H, J=10.30 Hz), 2.33 (d, 2H, J=13.28 Hz), 1.93 (t, 2H, J=10.30 Hz); $^{13}$C NMR ($CDCl_3$) δ 143.4, 138.1, 129.4, 129.1, 128.5, 127.4, 62.7, 53.2, 49.4, 36.2.

EXAMPLE 2

4-(Phenylamino)-1-(phenylimethyl)-4-piperidinecarboxamide, 2

Aminonitrile 1 (2.0 g, 6.86 mmol) was dissolved in 11 mL of trifluoroacetic acid under a nitrogen atmosphere. Sulfuric add (2.7 mL) was added dropwise. The light brown solution was stirred at 45-50° C. for 16 h. The reaction mixture was cooled to room temperature and slowly poured into an ammonium hydroxide 40 mL/ice mixture. The solution was filtered and the solids were collected to give 1.73 g of amide 2 in an 82% yield. mp 179-182° C.; $^1$H NMR (CDCl$_3$) δ 7.33-7.16 (m, 5H), 6.89 (br s, 1H), 6.78 (t, 1H, J=7.33 Hz), 6.63 (d, 2H, J=7.33 Hz), 5.48 (s, 1H), 4.05 (s, 1H), 2.77-2.71 (m, 2H), 2.37-2.30 (m, 2H), 2.10 (t, 2H, J=11.9 Hz), 1.95 (br d, 2H, J=13.28 Hz); $^{13}$C NMR (CDCl$_3$) δ 178.7, 143.8, 138.3, 129.3, 129.1, 129.0, 128.3. 127.2, 119.3, 116.2, 63.1, 58.3, 48.8, 31.4.

EXAMPLE 3

1-(phenylmethyl)-4,4-(2-phenyl-2,4-diaza-4-oxo-cyclopentane)piperidine, 3

Amide 2 (15.00 g, 48.48 mmol), dimethylformamide dimethoxyacetal (17.30 g, 145.0 mmol), and 50 mL of methanol were heated at 55° C. for 16 h. The volatiles were evaporated. The residue was recrystallized from toluene to yield 13.84 g of compound 3 in an 89% yield. mp 169-170° C.; $^1$H NMR (CDCl$_3$) δ 8.22 (s, 1H), 7.49-7.45 (m, 3H), 7.28-7.16 (m, 7H), 3.57 (br s, 2H), 3.10-2.95 (m, 2H), 2.75-2.58 (m, 2H), 2.10-1.92 (m, 2H), 1.79 (br d, 2H, J=13.28 Hz); $^{13}$C NMR (CDCl$_3$) δ 194.1, 169.2, 138.4 135.4, 139.1, 129.7, 129.3, 128.4, 128.1, 127.2, 65.0, 62.7, 46.9, 30.9.

EXAMPLE 4

Methyl 4-(phenylamino)-1-(phenylmethyl)-4-piperidinecarboxylate, 4

Cyclized intermediate 3 (11.00 g, 33.44 mmol) and sulfuric acid (4.6 g) were sequentially dissolved in 300 mL of methanol in a pressure bottle. The bottle was sealed and the mixture was heated at 95° C. for 16 h. The volatiles were evaporated. The residue was neutralized with a saturated sodium carbonate solution and extracted three times with chloroform. The combined organic extracts were washed with brine. The organic solution was dried with sodium sulfate, filtered and volatiles were evaporated. The residue was converted to the oxalate salt in isopropanol to provide 13.60 g of compound 8 in a 95% yield. mp 160-162° C.; $^1$H NMR (CD$_3$OD) δ 7.50-7.44 (m, 5H), 7.11-7.07 (m, 2H), 6.70 (t, 1H, J=7.33 Hz), 6.59 (d, 2H, J=7.79 Hz), 4.32 (s, 2H), 3.62 (s, 3H), 3.38-3.29 (m, 4H), 2.47-2.27 (m, 4H); $^{13}$C NMR (CD$_3$OD) δ 174.8, 165.4, 145.3, 131.1, 129.9, 129.1, 129.0, 128.7, 118.5, 115.0, 60.0, 56.4, 51.7, 29.8.

This chemistry can be applied to 1-phenylethyl-4-piperidinone for a more direct route to Carfentanil via anilino methyl ester 8, as shown below.

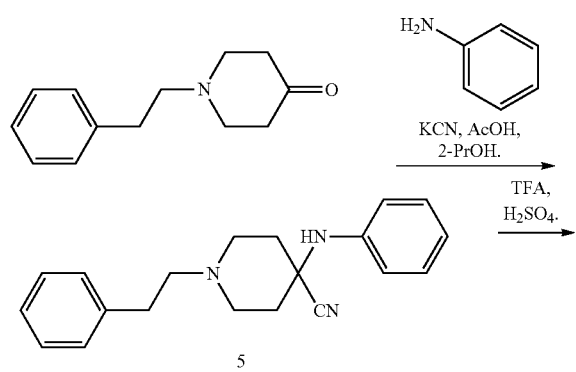

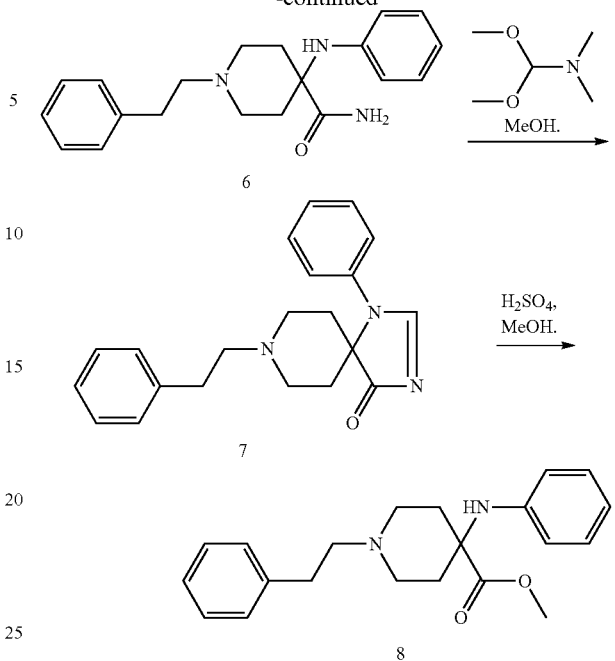

EXAMPLE 5

4-(Phenylamino)-1-(phenylethyl)-4-piperidinenitrile, 5

1-Phenylethyl-4-piperidinone (13.92 g, 68.6 mmol), aniline (8.94 g, 96 mmol), and potassium cyanide (6.25 g, 96 mmol) were added to 130 mL of isopropanol and cooled in an ice bath. Acetic acid (14.61 mL) was added dropwise and the addition funnel was washed with 15 mL of isopropanol. The mixture was heated at reflux overnight. The mixture was allowed to cool and poured over a 60 mL ammonium hydroxide/ice mixture. The mixture was stirred and then was extracted three times with chloroform. The combine chloroform extracts were washed with brine. The organic solution was dried with MgSO$_4$, filtered, and the volatiles were evaporated. The residue was recrystallized from 35 mL of isopropanol to provide a tan solid in an 80% yield. mp 176-178° C.; $^1$H NMR (CDCl$_3$) δ 7.31-7.19 (m, 7H), 6.94-6.90 (m, 3H), 3.65 (s, 1H), 2.92-2.89 (m, 2H), 2.81-2.78 (m, 2H), 2.69-2.66 (m, 2H), 2.55-2.49 (m, 2H), 2.39-2.35 (m, 2H), 1.98-1.91 (m, 2H); $^{13}$C NMR (CDCl$_3$) δ 143.3, 140.1, 129.4, 128.8, 128.5, 126.2, 121.1, 120.7, 119.9, 60.0, 53.2, 49.4, 36.2, 33.8.

EXAMPLE 6

4-(Phenylamino)-1-(2-phenylethyl)-4-pipenidinecarboxamide, 6

Aminonitrile 5 (2.0 g, 6.55 mmol) was dissolved in 10 mL of trifluoroacetic acid under a nitrogen atmosphere. Sulfuric acid (2.6 mL) was added dropwise. The light brown solution was stirred at 45-50° C. for 16 h. The reaction mixture was cooled to room temperature and slowly poured into an ammonium hydroxide (40 mL/ice mixture. The solution was extracted with chloroform three times. The combined organic extracts were washed with brine. The organic solution was dried with sodium sulfate, filtered and volatiles were evaporated. The resulting light brown solid was recrystallized from toluene to give the 1.52 g of amide 2 in a 72% yield. mp 178-180° C.; $^1$H NMR (CDCl$_3$) ∂ 7.29-7.17 (m, 7H), 6.88 (br s, 1H), 6.81 (t, 1H, J=7.33 Hz), 6.64 (d, 2H, J=7.79 Hz), 5.44 (s, 1H), 4.02 (s, 1H), 2.86 (dt, 2H, J=12.36 Hz, 3.42 Hz), 2.80-2.76 (m, 2H), 2.60-2.56 (m, 2H), 2.39-2.31 (m, 2H), 2.16 (t, 2H, J=11.23 Hz), 1.97 (d, 2H, J=12.82 Hz); $^{13}$C NMR (CDCl$_3$) δ 178.4, 143.7, 140.4, 129.3, 128.8, 128.5, 126.2, 119.4, 116.2, 60.6, 58.3, 48.8, 33.8, 31.5.

EXAMPLE 7

1-(2-phenylethyl)-4,4-(2-phenyl-2,4-diaza-4-oxo-cyclopentane)piperidine, 7

Amide 6 (1.4 g, 4.33 mmol), dimethylformamide dimethoxyacetal (1.55 g, 13.0 mmol), and 50 mL of methanol were heated at 55° C. for 16 h. The volatiles were evaporated. The residue was recrystallized from toluene to yield 1.35 g of compound 7 in a 94% yield. mp 197-200° C.; $^1$H NMR (CDCl$_3$) δ 8.25 (s, 1H), 7.49-7.45 (m, 3H), 7.28-7.15 (m, 7H), 3.21-3.05 (m, 2H), 2.83-2.61 (m, 8H), 2.11-1.96 (m, 2H), 1.84 (d, 2H, J=13.28 Hz); $^{13}$C NMR (CDCl$_3$) δ 194.0, 169.3, 140.0, 135.2, 130.1, 129.7, 128.7, 128.5, 128.1, 126.2, 64.8, 60.0, 46.8, 33.7, 30.7.

EXAMPLE 8

Methyl 4-(phenylamino)-1-(2-phenylethyl)-4-piperidinecarboxylate, 8

Cyclized intermediate 7 (1.3 g, 3.9 mmol) and sulfuric acid (0.5 g) were dissolved in 40 mL of methanol in a pressure bottle. The bottle was sealed and the mixture was heated at 95° C. for 16 h. The volatiles were evaporated. The residue was neutralized with a saturated sodium carbonate solution and extracted three times with chloroform. The combined organic extracts were washed with brine. The organic solution was dried with sodium sulfate, filtered and volatiles were evaporated. The residue was converted to the oxalate salt and was recrystallized from ethanol to provide 1.10 g of compound 8 in a 66% yield. mp 234-236° C.; $^1$H NMR (D$_6$-DMSO) δ 7.28-7.15 (m, 5H), 7.03 (t, 2H, J=7.55 Hz), 6.55 (t, 1H, J=7.11 Hz), 6.48 (d, 2H, J=7.79 Hz), 5.99 (br s, 1H), 3.57 (s, 3H), 2.98-2.70 (m, 8H), 2.15-2.08 (m, 4H); $^{13}$C NMR (D$_6$-DMSO) δ 175.8, 165.3, 146.3, 139.3, 129.4, 129.2, 128.9, 126.8, 117.3, 114.3, 58.5, 57.1, 52.8, 48.3, 31.8, 31.2.

The invention is a new conversion of anilino nitrile to the aniline methyl ester, not seen in the patent or open literature. The advantages of this transformation are conversion of nitrile to the amide with a better process in the N-phenylmethyl or N-phenethyl piperidine series. The transformation from amide to the spiro intermediate provides a milder alternative than the conversion of the amide to carboxylic acid, seen in the literature. The reaction does not require strongly basic conditions and the work-up and purifications are more efficient and simpler. The conversions of the spiro intermediates to the aniline methyl esters are also very efficient and mild.

The invention claimed is:

1. A process of making 4-(phenylamino)-1-(phenylalkyl)-4-piperidinecarboxamide, by converting in sequence:
    a) 1-phenylalkyl-4-piperidinone to 4-(phenylamino)-1-(phenylalkyl)-4-piperidinenitrile; and
    b) said 4-(phenylamino)-1-(phenylalkyl)-4-piperidinenitrile, to 4-(phenylamino)-1-(phenylalkyl)-4-piperidinecarboxamide, by reaction in trifluoroacetic acid solvent with non-aqueous sulfuric acid, said phenylalkyl being phenylmethyl or phenylethyl.

2. The process of claim 1, wherein said 1-(phenylalkyl)-4-piperidinone is reacted with aniline and KCN to form said 4-(phenylamino)-1-(phenylalkyl)-4-piperidinenitrile.

3. The process of claim 1, wherein said sulfuric acid and said trifluoroacetic acid are provided in a molar ratio of about 1:2 to about 1:10.

4. The process of claim 3, wherein said sulfuric acid and said trifluoroacetic acid are provided in a molar ratio of about 1:4.

5. The process of claim 1, wherein said phenylalkyl is phenylethyl.

* * * * *